United States Patent [19]
Pearce

[11] 3,939,221
[45] Feb. 17, 1976

[54] XYLENES SEPARATION PROCESS
[75] Inventor: David Pearce, Virginia Water, England
[73] Assignee: The British Petroleum Chemical International Ltd., London, England
[22] Filed: July 23, 1974
[21] Appl. No.: 490,936

[30] Foreign Application Priority Data
July 27, 1973 United Kingdom............... 35842/73

[52] U.S. Cl..... 260/674 SA; 260/668 A; 260/674 A
[51] Int. Cl.² .......................................... C07C 7/13
[58] Field of Search....... 260/674 A, 674 SA, 668 A

[56] References Cited
UNITED STATES PATENTS

| | | | |
|---|---|---|---|
| 2,926,206 | 2/1960 | Schaeffer et al..................... | 260/674 |
| 3,504,047 | 3/1970 | Haresnape .......................... | 260/674 |
| 3,504,048 | 3/1970 | Rosset................................. | 260/674 |
| 3,636,180 | 1/1972 | Broughton .......................... | 260/674 |
| 3,707,550 | 12/1972 | Stine et al............................ | 260/674 |
| 3,813,452 | 5/1974 | Bieser................................. | 260/674 |

Primary Examiner—Delbert E. Gantz
Assistant Examiner—C. E. Spresser
Attorney, Agent, or Firm—Morgan, Finnegan, Pine, Foley & Lee

[57] ABSTRACT

A continuous process for the separation of a mixed xylene isomer feedstock into o - and p - isomer fractions by feeding the mixed xylene isomer feedstock to a fractional distillation column in which a fraction containing a major portion of the o-xylene in the feedstock is removed from the bottom of the column and further fractionated to recover substantially pure o-xylene and a major portion of the p-xylene in the feedstock is removed as an overhead fraction, the p-xylene being removed from the overhead fraction by crystallisation and the mother liquor therefrom being recycled to the feed after contact with an isomerisation catalyst the improvement which comprises contacting the mother liquor remaining after crystallization of p-xylene, together with additional mother liquor, with a substrate active for the selective adsorption of p-xylene and thereafter recovering the adsorbed p-xylene from said substrate, the amount of mother liquor added being substantially equal to the quantity of p-xylene recovered from the adsorptive substrate in any given time.

11 Claims, 1 Drawing Figure

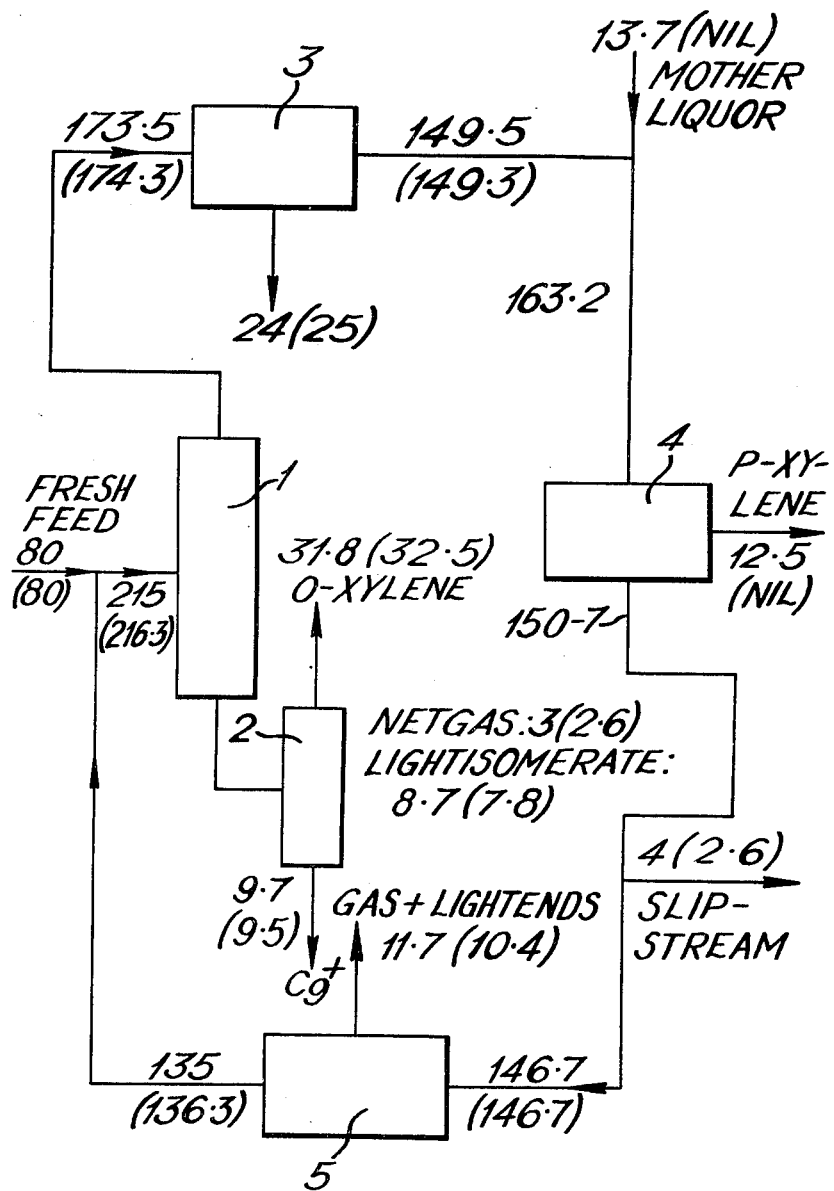

XYLENES SEPARATION PROCESS

The present invention relates to an improved process for the separation or ortho- and para-isomers of xylene.

A known method of separating a $C_8$ heart-cut fraction from catalytic reformate into o- and p-isomers of xylene is to pass the $C_8$ fraction to an isomer splitter, taking an o-xylene rich stream from the bottom of the splitter and further fractionally distilling this fraction to produce a substantially pure o-xylene product. The overhead fraction from the isomer splitter, containing essentially p- and m-xylenes and ethylbenzene, are passed to a freeze plant where high purity p-xylene is extracted by crystallisation. The mother liquor in some plants is passed directly to the gasoline pool and in other plants is recycled to the feed-point after contact with an isomerisation catalyst when the composition of the liquor is restored to approximate that of the initial feedstock after the removal of gas and light ends.

It is a disadvantage of this method of separating p-xylene that the extraction efficiency in the freeze plant is limited by the eutectic point of the feed to the freeze plant. A maximum extraction efficiency of approximately 60% is typical of commercial operation. Consequently in those plants operating without an isomerisation unit a significant quantity of p-xylene (30-50% weight of that present in the feed) passes to the gasoline pool in the mother liquor stream.

It has now been found that the yield of p-xylene from a xylene complex incorporating an isomerisation unit is increased by the addition of a selective adsorption unit.

Thus, in a continuous process for the separation of a feedstock containing a major proportion of mixed xylene isomers into substantially pure o- and p-isomer fractions by feeding the feedstock to a fractional distillation column in which a fraction containing a major portion of the o-xylene in the feedstock is removed from the bottom of the column and further fractionated to recover substantially pure o-xylene and a major portion of the p-xylene in the feedstock is removed in an overhead fraction, the p-xylene being removed from the overhead fraction by crystallisation and the mother liquor therefrom being recycled to the feed after contact with an isomerisation catalyst the improvement which comprises contacting the mother liquor remaining after crystallisation of p-xylene with a substrate active for the selective adsorption of p-xylene and thereafter recovering the absorbed p-xylene from said substrate.

It is preferred to use as feedstock a $C_8$ heart-cut derived from a catalytic reformate though other fractions containing the mixed isomers may be used. The composition of a typical $C_8$ heart-cut is as follows: benzene (0.2%), toluene (2.3%), $C_8$ naphthene (0.0%), ethyl benzene (15.2%), p-xylene (17.5%), m-xylene (40.0%), o-xylene (17.3%), $C_9$ aromatics (7.4%) and $C_9$ naphthenes (0.1%), all percentages being expressed by weight.

Whilst any substrate which selectively adsorbs p-xylene may be used in the process of the invention it is preferred to use molecular sieves.

The term molecular sieve normally implies an adsorbant which depends for its mode of operation on differences in the size of molecules contacted therewith but in this specification the conventional meaning is extended further to include adsorbents depending for their action on the physico-chemical attraction of different isomer configurations.

Molecular sieves are crystalline alumino-silicates which may be naturally occurring or synthetically produced. Particular crystalline alumino-silicates encompassed by the present invention include alumino-silicate cage structures in which the alumina and silica tetrahedra are intimately connected in an open three dimensional network. The tetrahedra are cross-linked by the sharing of oxygen atoms with spaces between the tetrahedra occupied by water molecules prior to partial or total dehydration of the alumino-silicate. The dehydration of this alumino-silicate results in crystals interlaced with cells having molecular dimensions.

In a hydrated form the crystalline alumino-silicates generally encompass those zeolites represented by the formula:

$$M_{2/n}O : Al_2O_3 : w\ SiO_2; y\ H_2O \qquad (I)$$

wherein M is a cation which balances the electrovalence of the tetrahedra and is generally referred to as an exchangeable cationic site, n represents the valence of the cation, w represents the number of moles of $SiO_2$ and y represents the number of moles of water.

Within the formula (I) above the alumino-silicate may be of the type X structure or the type Y structure. The type X structured alumino-silicates can be represented in terms of mole oxides as represented by the formula:

$$0.9 \pm 0.2 M_{2/n}{}^1O : Al_2O_3 : 2.5 \pm 0.5\ SiO_2 : y\ H_2O \qquad (II)$$

Where $M^1$ represents at least one cation having a valence of not more than 3, n represents the valence of $M^1$ and y has a value of up to about 9 depending upon the identity of $M^1$ and the degree of hydration of the crystalline structure.

The type Y structure alumino silicates can be represented in terms of the mole oxides for the sodium form by the formula:

$$0.9 \pm 0.2\ Na_2O : Al_2O_3 : w\ SiO_2 : y\ H_2O \qquad (III)$$

where w has a value of greater than about 3 up to 8 and y may be any value up to about 9.

The terms type X structure and type Y structure alumino-silicates include all alumino-silicates having a general structure as represented in U.S. Pat. No. 2,882,244 and U.S. Pat. No. 3,130,007 and in particular materials obtained from such an alumino-silicate by partial or complete replacement of the cation $M^1$ in the formula (II) or sodium in the formula (III) with other individual cations or groups of cations.

Cationic or base exchange methods are generally known to those familiar with the art of crystalline alumino-silicate production and are generally performed by contacting the alumino-silicate with an aqueous solution of soluble salts of the cation or cations desired to be exchanged on to the alumino-silicate. The desired degree of exchange takes place before the sieves are removed from the aqueous solution, washed and dried to the desired water content. An individual solution of the desired cation may be contacted with the alumino-silicate or an exchange solution containing a mixture of cations with the alumino-silicate.

Cations which may suitably be exchanged on to the alumino-silicate comprise one or more cations of metals of Groups IA, IIA and IB of the Periodic Table. It is preferred to exchange on to the alumino-silicate one or more cations of lithium, sodium, potassium, rubidium, cesium, beryllium, magnesium, calcium, strontium, barium, silver, manganese, cadmium, and copper. Preferred combinations of cations comprise potassium and barium, potassium and beryllium, potassium and manganese, rubidium and barium, cesium and barium, copper and cadmium, copper and silver, zinc and silver and copper and potassium. Especially preferred cations comprise potassium, barium, sodium and silver and especially preferred combinations of cations are potassium and barium, potassium and beryllium, potassium and cesium, barium and rubidium, cesium and barium, and copper and potassium.

When single cations are base-exchanged upon an alumino-silicate the cation may comprise between 5 and 75 weight per cent of the alumino-silicate. The percentage based on the volatile free basis, generally expressed as VF, is the percentage of the material upon the alumino-silicate after it has been exposed to an inert gas purge at 500°C for a time period to allow it to reach a constant weight. When single ions are exchanged on to the alumino-silicate this cation may be ion-exchanged from the alumino-silicate to place anywhere from 1 per cent up to 100 per cent of the original cations present (generally sodium or calcium) upon the alumino-silicate prior to its being ion-exchanged. By knowing the empirical formula including the silica/alumina ratio of the alumino-silicate used, its water content and the percentage of binder, if any, it is possible to calculate, after ion-exchanging, the percentage of ion-exchanging which has occurred.

When more than one cation is placed upon the alumino-silicate there are two parameters which can be varied in order to maximise its selectivity. The two parameters are the extent of ion-exchange and the ratio of individual cations placed on the alumino-silicate. Where the cation pairs comprise a Group IIA metal and a Group IA metal the weight ratio of these two components upon the alumino-silicate may be in the range, 1 to 80 depending upon the molecular weight of the Group IIA or Group IA metal. A preferred alumino silicate is one which contains barium and potassium cations having a weight ratio of barium to potassium of 1 to 40, more preferably 1 to 30, and even more preferably 5 to 15. The cations may occupy from 20 to 100 percent of the ion-exchangeable sites located on the alumino-silicate. In some instances, substantially all of the original cations placed on the alumino-silicate may be removed therefrom by the cations exchanged.

Where a cation other than a cation of a Group IA or Group IIA metal is placed on the alumino-silicate from 10 to 100 weight percent of the original cations present on the alumino-silicate may be replaced by these metals.

The adsorbed p-xylene may be recovered from the substrate by any means known in the art. Suitable methods of recovering p-xylene from its mixtures with other $C_8$ hydrocarbons by adsorption from the liquid phase are the Parex process described in Chemical Engineering Progress, Volume 6, No. 9, September 1970, pages 70 to 75, and the Aromax Process described in Petroleum & Petrochemical International, Volume 12, No. 12, pages 65 to 68.

In a preferred embodiment of the process the mother liquor remaining after crystallisation is combined with additional mother liquor prior to contact with the substrate active for the selective adsorption of p-xylene, the amount of mother liquor added being substantially equal to the quantity of p-xylene recovered from the adsorptive substrate in any given time. The additional mother liquor may suitably be obtained from a second or any number of xylene separation plants using the crystallisation method for isolating p-xylene in the absence of a selective adsorption and/or an isomerisation step. Thus this embodiment of the invention affords a method of increasing the capacity of a conventional xylenes plant without increasing the size of the freeze unit, thus economising on plant costs, at the same time increasing the p-xylene extraction efficiency of one or more xylene plants not incorporating an adsorption unit and additionally increasing the p-xylene make by isomerisation. The increase in capacity is achieved without modification to the existing conventional xylenes plant, other than the addition of an adsorption unit, because the quantity of feed to the isomerisation unit and the input to the other units remain substantially the same.

In order to maintain the total feed to the fractional distillation column separating o- and p-xylene constant whilst increasing the individual xylenes make, without combining additional mother liquor with the mother liquor remaining after crystallisation, it is necessary to increase the amount of feedstock to the fractional distillation column, since the recycle stream exiting from the isomerisation unit is diminished.

The invention will now be described with reference to the FIGURE which illustrates a process flow-sheet complete with approximate material balance figures, the figures in brackets being the material balance in the absence of the adsorption unit.

A $C_8$ heart-cut fraction from catalytic reformate containing o-, m- and p-isomers of xylene in addition to ethyl benzene and minor constituents is fed to a fractional distillation column 1 where a bottoms fraction containing a major portion of o-xylene is removed and fed to a second fractional distillation column 2 from which substantially pure o-xylene is removed overhead and a $C_9^+$ fraction is removed from the bottom. The overhead fraction from fractional distillation column 1 passes to a freezer unit 3 in which pure p-xylene is crystallised out at a temperature above the entectic point and removed. The mother liquor remaining is combined with a further quantity of mother liquor from a plant operating on the crystallisation principle but not having adsorption or isomerisation units. The combined mother liquor, containing up to 10% p-xylene, is passed to an adsorption unit 4 e.g. operating the Parex process which unit selectively adsorbs p-xylene to the extent that only 2% remains in the liquor exiting from the unit. The p-xylene depleted liquor is passed to the isomerisation unit 5 (e.g. an Octafiner unit packed with an Engelhard Industries noble metal isomerisation catalyst) wherein the composition of the liquor is adjusted to approximate the original feed to the fractional distillation column 1 after gas plus light ends are removed.

From an examination of the approximate material balance given in the Figure and the following Table it will be seen that from 80t/a of heart-cut reformate an additional 11.5t/a of p-xylene is produced at the expense of only 0.7t/a of o-xylene by combining 13.7t/a of mother liquor from another plant with the feed to the adsorption unit without substantially changing the load on the other units.

TABLE

|  | Material Balance (t/a) | | |
| --- | --- | --- | --- |
|  | Without adsorption unit | With adsorption unit | Δ |
| Heart cut | 80.0 | 80.0 | nil |
| Mother liquor added | nil | 13.7 | 13.7 |

TABLE-continued

| | Material Balance (t/a) | | |
|---|---|---|---|
| | Without adsorption unit | With adsorption unit | Δ |
| from 2nd plant | 80.0 | 93.7 | 13.7 |
| p-xylene | 25.0 | 36.5 | +11.5 |
| o-xylene | 32.5 | 31.8 | − 0.7 |
| Net gas | 2.6 | 3.0 | + 0.4 |
| Light isomerate | 7.8 | 8.7 | + 0.9 |
| Heavy Ends | 9.5 | 9.7 | + 0.2 |
| Slipstream | 2.6 | 4.0 | + 1.4 |
| | 80.0 | 93.7 | +13.7 |

I claim:

1. In a continuous process for the separation of a feedstock containing a major proportion of mixed xylene isomers into substantially pure o- and p-isomer fractions by feeding the feedstock to a fractional distillation column in which a fraction containing a major portion of the o-xylene in the feedstock is removed from the bottom of the column and further fractionated to recover substantially pure o-xylene and a major portion of the p-xylene in the feedstock is removed in an overhead fraction, the p-xylene being removed from the overhead fraction by crystallization and the mother liquor therefrom being recycled to the feed after contact with an isomerization catalyst, the improvement which comprises, prior to contacting said mother liquor remaining after crystallization with an isomerization catalyst, the steps of combining said mother liquor with additional mother liquor and contacting said combined mother liquor with a crystalline alumino-silicate active for the selective adsorption of p-xylene the hydrated form of which has the formula:

$$M_{2/n}O : Al_2O_3 : wSiO_2 : yH_2O \qquad (I)$$

wherein M is a cation which balances the electrovalance of the tetrahedra, $n$ represents the valence of the cation, $w$ represents the number of moles of $SiO_2$ and $y$ represents the number of moles of water;

and, thereafter recovering the adsorbed p-xylene from said substrate, the amount of said mother liquor added being substantially equal to the quantity of p-xylene recovered from said crystalline alumino-silicate in any given time.

2. A process according to claim 1 wherein said feedstock is a $C_8$ heartcut derived from a catalytic reformate.

3. A process according to claim 1 wherein said crystalline alumino-silicate is selected from type X structured zeolite represented in terms of mole oxides by the formula:

$$0.9 \pm 0.2 M_{2/n}{}^1 O : Al_2O_3 : 2.5 \pm 0.5\ SiO_2 : yH_2O \qquad (II)$$

wherein $M^1$ represents at least one cation having a valence of not more than 3, $n$ represents the valence of $M^1$ and $y$ has a value of up to about 9 and type Y structured zeolites represented in terms of mole oxides by the formula:

$$0.9 \pm 0.2 Na_2O : Al_2O_3 : wSiO_2 : yH_2O \qquad (III)$$

where $w$ has a value of greater than about 3 up to 8 and $y$ has a value of up to 9.

4. A process according to claim 1 wherein said cation M in crystalline alumino-silicate of formula (I) is replaced with at least one cation of metals selected from Groups IA, IIA or IB of the Periodic Table.

5. A process according to claim 1 wherein said cation M in said crystalline alumino-silicate of formula (I) is replaced with at least one cation of metals selected from lithium, sodium, potassium, rubidium, cesium, beryllium mangnesium, calcium, strontium, barium, silver, manganese, cadmium and copper.

6. A process according to claim 1 wherein said cation M in said crystalline alumino-silicate of formula (I) is replaced with a combination of cations of metals selected from the pairs potassium and barium, potassium and beryllium, potassium and manganese, potassium and rubidium, potassium and cesium, rubidium and barium, cesium and barium, copper and cadmium, copper and silver, zinc and silver and copper and potassium.

7. A process according to claim 1 wherein said cation M in said crystalline alumino-silicate of formula (I) is replaced by a single cation of a metal selected from potassium, barium, sodium and silver in an amount between 5 and 75 weight percent of the alumino-silicate.

8. A process according to claim 1 wherein said cation M in said crystalline alumino-silicate of formula (I) is replaced by a combination of a cation of a metal selected from Group IIA of the Periodic Table with a cation of a metal selected from Group IA of the Periodic Table in a weight ratio of 1 to 80.

9. A process according to claim 1 wherein said cation M in said crystalline alumino-silicate formula (I) is replaced by a combination of the cations of barium and potassium in a weight ratio of barium to potassium of 1 to 40.

10. A process according to claim 9 wherein said weight ratio of barium to potassium is 5 to 15.

11. A process according to claim 1 wherein said additional mother liquor is obtained from at least one xylene isomer separation plant using only crystallization for separating p-xylene.

* * * * *

UNITED STATES PATENT AND TRADEMARK OFFICE
CERTIFICATE OF CORRECTION

PATENT NO. : 3,939,221
DATED : February 17, 1976
INVENTOR(S) : David Pearce

It is certified that error appears in the above-identified patent and that said Letters Patent are hereby corrected as shown below:

First page, left hand column, lines 4-5 [73], change name of Assignee from

"The British Petroleum Chemical International Ltd., London, England"

to

- - BP California Limited, London, England - -

Signed and Sealed this

Ninth Day of November 1976

[SEAL]

Attest:

RUTH C. MASON
Attesting Officer

C. MARSHALL DANN
Commissioner of Patents and Trademarks